(12) United States Patent
Burdick

(10) Patent No.: US 7,109,358 B2
(45) Date of Patent: Sep. 19, 2006

(54) PROCESS FOR THE PREPARATION OF ISOFLAVONES

(75) Inventor: David Carl Burdick, Peoria, IL (US)

(73) Assignee: DSM IP Assets B.V., Heerlen (NL)

( * ) Notice: Subject to any disclaimer, the term of this patent is extended or adjusted under 35 U.S.C. 154(b) by 369 days.

(21) Appl. No.: 10/474,418

(22) PCT Filed: Apr. 19, 2002

(86) PCT No.: PCT/EP02/04319

§ 371 (c)(1),
(2), (4) Date: Mar. 11, 2004

(87) PCT Pub. No.: WO02/085881

PCT Pub. Date: Oct. 31, 2002

(65) Prior Publication Data

US 2004/0158082 A1  Aug. 12, 2004

(30) Foreign Application Priority Data

Apr. 25, 2001 (EP) ................... 01110212

(51) Int. Cl.
*C07D 311/36* (2006.01)

(52) U.S. Cl. .................................................... 549/403
(58) Field of Classification Search ................ 549/403
See application file for complete search history.

(56) References Cited

OTHER PUBLICATIONS

V.G. Pivovarenko, et al., "Acetoformic Anhydride in the Synthesis of Chromones. 1. Synthesis of 3-Hetarylchromones", *Chem. Heterocycl. Compd.* vol. 27, No. 5, pp. 496-501 (1991).
V.G. Pivovarenko, et al., "Mixed Anhydride of Acetic and Formic Acids in the Synthesis of Chromones. 2. Synthesis of 3-Arylchromones", *Chem. Heterocycl. Compd.* vol. 28, No. 5, pp. 497-502 (1992).
V.G. Pivovarenko, et al., "Effective Synthesis of 7-Hydroxyisoflavone O-Glucosides", *Chem. Nat. Compd.* vol. 24, No. 4, pp. 432-438 (1988).

*Primary Examiner*—Taofiq Solola
(74) *Attorney, Agent, or Firm*—Bryan Cave LLP

(57) ABSTRACT

The invention relates to a process for the preparation of 2H-isoflavones which process comprises the reaction of a 2-hydroxyaryl alkyl ketone in the presence of a base with a formic-sulfuric anhydride salt which reaction is followed by neutralization. The procedure is especially suitable for the preparation of genistein.

18 Claims, No Drawings

PROCESS FOR THE PREPARATION OF ISOFLAVONES

This application is the National Stage of International Application No. PCT/EP02/04319, filed Apr. 19, 2002.

Disclosed is a process for the preparation of isoflavones from 2-hydroxyaryl alkyl ketones which is suitable for chemical manufacturing. Of particular interest are 5,7-dihydroxyisoflavones such as genistein.

Isoflavones are characterized by the general benzopyranone structure 1.

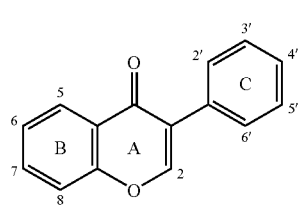

Structure 1

Many substances containing this ring structure are found naturally, mainly in *Leguminosae* (*Fabaceae*), the richest sources being soya, lentils, chick pea, fenugreek, clovers, alfalfa, and various types of beans. Most frequently, the isoflavones are substituted on the rings to varying degrees with hydroxyl, alkoxyl, prenyl and prenyl-derived groups and the substructure may be embedded in more complex ring structures. Natural isoflavones are often substituted at the hydroxyl groups with sugars, which are sometimes additionally substituted by ester groups. It is common to find isoflavones as mixtures of closely related substances. For example, the isoflavones of soybeans include genistein, daidzein, glycitein, formononetin and biochanin A which occur co-mixed as free aglycones as well as their glycosides in approximately 500–3000 ppm based on dry weight. Direct isolation of isoflavones from biomass containing such mixtures is thus complex and often largely economically impractical in many cases.

There exists a need for a process capable of providing on manufacturing scale pure isoflavones substituted by hydrogen at the 2-position. It is the object of this invention to disclose such a process. This procedure is especially suitable for a the preparation of 2H-isoflavones with polyhydroxyl substitution, for example 5,7-dihydroxy-isoflavones such as genistein, which are more difficult to obtain in an industrially practical manner, said 2H-isoflavones being prepared in high yield and with a high degree of purity.

The present invention relates to a process for the preparation of 2H-isoflavones of formula I

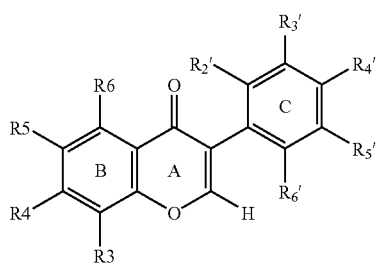

formula I wherein

R3 is hydrogen, hydroxyl or alkoxyl, alkyl, substituted alkyl, or unsaturated alkyl, when R3 is not hydrogen or hydroxyl then the atoms comprising the substituent may comprise a heterocyclic ring of oxygen and carbon atoms attached to position 4 of the ring which rings may be saturated or unsaturated and optionally substituted with alkyl groups;

R4 is hydrogen, hydroxy or alkoxyl, when R4 is alkoxyl then the elements of the substituent may comprise a heterocyclic ring of carbon and oxygen atoms attached to positions 3 or 5 which may be saturated or unsaturated and optionally substituted with alkyl groups;

R5 is hydrogen, hydroxyl, alkoxyl, alkyl, substituted alkyl, or unsaturated alkyl, when R5 is not hydrogen or hydroxyl then the atoms of the substituent may comprise a heterocyclic ring of carbon and oxygen atoms attached to the ring at position 4 to form saturated or unsaturated rings such as methylenedioxy or dihydrofuran, dihydropyran, or pyrene rings which rings themselves may be substituted with alkyl groups;

R6 is hydrogen, hydroxyl, alkoxyl, alkyl or substituted alkyl;

R2' is hydrogen, hydroxyl, alkoxyl, alkyl, substituted alkyl, or unsaturated alkyl;

R3' is hydrogen, hydroxyl, alkoxyl, alkyl, substituted alkyl or unsaturated alkyl, when R3' is not hydrogen or hydroxyl, the atoms of the substituent may comprise a heterocyclic ring of carbon and oxygen atoms attached to position 2' or 4' which ring may be saturated or unsaturated and may be substituted with alkyl groups;

R4' is hydrogen, hydroxyl, or alkoxyl, when R4' is not hydrogen or hydroxyl the elements of the substituent may comprise a heterocyclic ring of carbon and oxygen which are attached to position 3' or 5', which ring may be saturated or unsaturated and is optionally substituted with alkyl groups;

R5' is hydrogen, hydroxyl, alkoxyl, alkyl, substituted alkyl or unsaturated alkyl, when R5' is not hydrogen or hydroxyl, the atoms of the substituent may comprise a heterocyclic ring of carbon and oxygen atoms attached to position 4', which ring may be saturated or unsaturated and may be substituted with alkyl groups;

R6' is hydrogen, hydroxyl, alkoxyl, alkyl, substituted alkyl, or unsaturated alkyl;

which process comprises the reaction of a 2-hydroxyaryl alkyl ketone of formula II

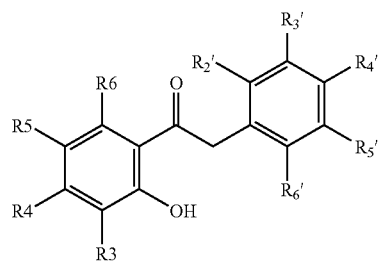

formula II wherein the substituents have the meaning as defined above, in the presence of a base with a formic-sulfuric anhydride salt of formula III

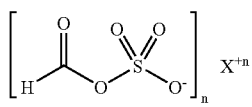

formula III wherein
X is a metallic cation, ammonium, an amine salt, salt of a heterocyclic base, quaternary ammonium or phosphonium salt including polymeric or polymer bound forms thereof;
n is an average number of 1 to 4, and which reaction is followed by neutralization.

When a substituent other than R6 is hydroxyl, or contains a hydroxyl group, it is understood that one or more of the free hydroxyl positions in such ketones may remain unprotected, or, if desired, may be protected in the usual manner with appropriate protecting groups, including but not limited to various ethers, esters, acetals or ketals such as are compatible with the reaction and purification conditions. Methods for their formation and removal are known to those skilled in the art, illustrative examples being found in the scientific literature (see, e.g., Protective Groups in Organic Synthesis, Green and Wuts, 3rd edition, John Wiley & Sons, 1999). These protected isoflavones can be used as intermediates for the preparation of more complex structures. It is, however, an attractive feature of this process that such protecting groups are not mandatory.

In one preferred embodiment of the present invention, "n" in formula III is 1 or 2.

The ketones as described above are useful precursors for the synthesis of isoflavones which are naturally occurring, as well as synthetic ones. Such ketones are available by known methods, including, but not limited to acylation of phenols with carboxylic acids, halides, anhydrides or nitrils or by rearrangements of phenol esters.

Bases are selected to maximize solubility of the ketone salt in the reaction solvent. Suitable bases include, but are not limited to metal carbonates, metal alkoxides, amines, heterocyclic bases, and quaternary ammonium or phosphonium alkoxides, including polymeric or polymer bound forms thereof. Preferred are the alkali metal carbonates, alkaline earth carbonates and tertiary alkyl amines. Most preferred are sodium or potassium carbonate and triethylamine.

In one aspect of the present invention, the base used for the process of this invention is selected from the group consisting of sodium carbonate, potassium carbonate, calcium carbonate, triethylamine, tributylamine, and di-isopropylethylamine.

The process of the present invention may be used to prepare isoflavones with various substituent patterns. The more preferred process involves the production of 5,7-dihdroxy isoflavones from 2,4,6-trihydroxyaryl alkyl ketones. These isoflavones are difficult to obtain on large scale by other procedures known in the art. Most preferred is a process for obtaining pure genistein.

Reagents to be used include, but are not limited to the alkali metal, alkaline earth or tertiary ammonium salts of formic-sulfuric anhydride. These may readily be prepared by reaction of anhydrous alkali metal, alkaline earth or tertiary ammonium formates with sulfur trioxide or sulfur trioxide complexes in a suitable solvent. Preferred are sodium, potassium, triethylammonium, tributylammonium, or di-isopropylethyl ammonium formates in reaction with the sulfur trioxide complex of dimethylformamide. A nearly stoichiometric amount of formate to sulfur trioxide is used but excess formate is not detrimental.

One embodiment of the present invention is related to a process wherein the counterion of the formic-sulfuric anhydride of formula III is selected from the group consisting of sodium, potassium, calcium, triethylammonium, tributylammonium or di-isopropylethyl ammonium.

One equivalent of base and one equivalent of formylating agent per acidic phenolic group on the ketone have given excellent conversions and yields in short reaction times. It is a desirable feature of this process that the excess of base and formylating agent may be reduced to less than the amount which would normally be required for complete formylation of all free acylable groups. The preferred amounts are determined empirically. With 2,4,6-trihydroxy ketones, it has been found possible to obtain good yields in acceptable reaction times using half to three quarters of theoretical amounts of base and formylating agents.

Reaction times of 30 minutes to 6 hours are in conformity with the present invention. Acceptable condensation temperatures of the present process are in the range of from −20° C. to +20° C. It is a desirable feature of this invention that the formylsulfate salts are substantially stable in the reaction media and may be held cold without significant loss of performance. When heated they undergo loss of carbon monoxide in a smooth, non-accelerating manner. Most preferred is an initial reaction temperature in the range of from −10° C. to +10° C. Under these conditions, reactions are completed within less than one to several hours but may be prolonged without loss of performance.

It is a desirable feature of this process that excess of formylating agent may safely be eliminated prior to workup by brief heating. For this purpose heating of the reaction mixture for 30 minutes to 1 hour is useful, at temperatures which are in the range of from 40° C. to 100° C. During the heating, other phenolic hydroxyl groups which may have been formylated are also regenerated, eliminating a hydrolytic step and reducing formate waste. The evolved carbon monoxide may be burned to relatively environmentally acceptable carbon dioxide.

Thus, the present invention is related to a process as defined above, wherein the process is performed at a temperature in the range of from −20° C. to +20° C., with an optionally heating of up to 100° C.

Solvents are selected to not reacting with the reagents and to maximize the solubility of the reactants. Complete solution of the reagents is not always necessary. Examples of such solvents are halocarbons, alcohols, ethers, esters, amides, and sulfones. Preferred are more polar solvents such as ethers, esters, and amides. When the bases and salts are amines, less polar solvents are useful. Most preferred solvents are amides such as dimethylformamide and N-methyl pyrrolidinone.

After conversion of the ketone to isoflavone has been accomplished, it is useful to first add to the reaction mixture sufficient acid to neutralize excess base prior to isolation. For this purpose sulfuric acid or bisulfate salts may be used in order to simplify the waste stream. The isoflavone may be isolated by separating it from the salts in a manner generally known to those skilled in the art, such as filtration or extraction, followed by crystallization.

In order to fully illustrate the nature of the invention and the manner of practicing the same, the following non-limiting examples are presented.

EXAMPLE 1

To a stirred suspension of 130 g anhydrous sodium formate (1.91 M) in 60 ml ethyl acetate at 20° C. was added 99 g acetyl chloride (1.26 M) and the white suspension stirred for 6 h. The mixture was filtered and the solids washed twice with 25 ml ethyl acetate. The combined filtrate and rinse were analyzed by 300 MHz proton NMR. Integration of peaks at 2.25, 8.75, and 9.1 gave the following composition in mol %: 3% acetic-anhydride, 3.5% formic anhydride, 30% formic-acetic anhydride. To 193 g of the above solution at −5° C. were added 22 g of 2,4,6-trihydroxyphenyl-4'-hydroxybenzyl ketone (84.5 mM) followed by a drop by drop addition of 118 g di-isopropylethylamine (1.01 M) over 60 min and the reaction stirred at −5° C. for 18 h. To the yellowish solution was added 100 ml hydrochloric acid (37%) and the mixture heated to 90° C. under 150 mbar vacuum to remove approximately 115 g of distillate. To the residue was added 225 ml water causing crystallization. The slurry was cooled, held at 0° C. for 30 min followed by filtration. The solids were rinsed twice with 100 ml water and dried at 25 mbar for 6 h at 60° C. to obtain a white powder (19.6 g). Quantitative HPLC analysis with external standards showed this to contain 97.3 wt. % genistein and 2.5 wt. % 2-methylgenistein. The yield of genistein is therefore 79% based on the ketone.

EXAMPLE 2

To 3.36 g triethylamine (33 mmol) in 20 ml dimethylformamide at 0° C. was added 1.52 g anhydrous formic acid (33 mmol) in 20 ml dimethylformamide. To this solution was added 5.05 g of a sulfur trioxide-dimethylformamide complex (33 mmol) in 15 ml dimethylformamide and the clear colorless solution stirred for 1 h at 0° C. to prepare triethylammonium formylsulfate. To 3.36 g triethylamine (33 mmol) and 2.92 g of 2,4,6-trihydroxyphenyl-4'-hydroxybenzyl ketone (11 mmol) in 22 ml dimethylformamide at 0° C. was added the triethylammonium formylsulfate solution, the mixture allowed to stir for 1 h, then heated for 1 h at 60° C. To the yellowish solution was added 21.5 ml sulfuric acid (36%) over 10 min, the reaction mixture distilled in vacuo at 25 mbar and 90° C. to remove solvents, then 117 ml water was added at 90° C. The resulting suspension was cooled over 3 h to 30° C., held 1 h, then filtered. The off-white solids were rinsed twice with water (20 ml each) then dried at 25 mbar overnight at 60° C. to furnish 2.26 g of product. HPLC analysis with external standards showed this to be composed of 97.6 wt. % genistein. The yield of genistein is therefore 74%. The mother liquors contained starting ketone corresponding to 18% of starting material.

EXAMPLE 3

To 3.36 g triethylamine (33 mmol) in 20 ml dimethoxyethane at 0° C. was added 1.52 g anhydrous formic acid (33 mmol) in 20 ml dimethoxyethane. To this solution was added 5.05 g of a sulfur trioxide-dimethylformamide complex (33 mmol) in 15 ml dimethoxyethane and the clear colorless solution stirred for 1 h at 0° C. to prepare triethylammonium formylsulfate. To 3.36 triethylamine (33 mmol) and 2.92 g of 2,4,6-trihydroxyphenyl-4'-hydroxybenzyl ketone (11 mmol) in 22 ml dimethoxyethane at 0° C. was added the triethylammonium formylsulfate solution, the mixture allowed to stir for 4 h at 0° C., then heated for 1 h at 60° C. To the mixture was added 30 ml sulfuric acid (30%), the reaction mixture distilled in vacuo at 25 mbar and 90° C. to remove solvents, then 58 ml water was added at 90° C. The resulting suspension was cooled over 3 h to 30° C., held 1 h, then filtered. The off-white solids were rinsed twice with water (20 ml each) then dried at 25 mbar overnight at 60° C. to furnish 2.54 g of off-white powdery product. HPLC analysis with external standards showed this to be composed of 88.8 wt. % genistein. The yield of genistein is therefore 76%. The mother liquors contained starting ketone corresponding to 17% of starting material.

EXAMPLE 4

To 3.43 g anhydrous sodium formate (50 mmol) in 50 ml dimethylformamide at 0° C. was added over 15 min 7.6 g of a sulfur trioxide-dimethylformamide complex (50 mmol) in 50 ml dimethylformamide and the mixture held at 0° C. for 1 h to form a solution of sodium formylsulfate. To this solution was added 3.32 g of 2,4,6-trihydroxyphenyl-4'-hydroxybenzyl ketone (12.5 mmol) followed by 6.36 g triethylamine (62.5 mmol) and the clear yellowish solution held for 2 h. To the mixture was added 7.4 ml hydrochloric acid (36%) and the suspension heated to 95° C. for 15 min. The cooled suspension was distilled in vacuo at 80° C. and 35 mbar to remove volatiles, then diluted with 133 ml water over 10 min. After 30 min at 0° C. the white suspension was filtered, the solids washed 3 times with water (50 ml each). The solids were dried at 60° C. and 25 mbar overnight to give 3.38 g of a beige powder. HPLC analysis showed this to be composed of 95 wt. % genistein. The yield of genistein is therefore 95%.

EXAMPLE 5

To 6.59 g anhydrous sodium formate (96 mmol) in 41 ml dimethylformamide at 0° C. was added 17.4 g of a sulfur trioxide-triethylamine complex (96 mmol) in 41 ml dimethylformamide and the mixture stirred for 4 h. A mixture of 6.37 g of 2,4,6-trihydroxyphenyl-4'-hydroxybenzyl ketone (24 mmol) and 10.23 g anhydrous sodium carbonate (96 mmol) in 58 ml dimethylformamide was stirred for 3 h, then the formylsulfate solution was added over 5 min. The reaction mixture was stirred for 18 h at 20° C., heated to 80° C. for 30 min, then 30 ml sulfuric acid (36%) was added and solvents removed in vacuo at 95° C. and 16 mbar. To the resultant slurry was added 255 ml water, the suspension stirred for 5 h at 20° C., filtered, and the solids were washed 3 times with water (50 ml each). The solids were dried at 60° C. and 15 mbar for 18 h to give 5.16 g of a beige product. HPLC analysis showed this to be composed of 98 wt. % genistein. The yield of genistein is therefore 72%. Analysis of the mother liquors showed the presence of ketone corresponding to 17% of the starting material.

EXAMPLE 6

To 103.5 g anhydrous sodium formate (1.5 mol) in 658 ml dimethylformamide at 0° C. was added 229.7 g of a sulfur trioxide-dimethylformamide complex (1.5 mol) in 658 ml dimethylformamide over 1 h and the reaction held for an additional hour to form a solution of sodium formylsulfate. To 159.8 g anhydrous sodium carbonate (1.5 mol) in 950 ml dimethylformamide was added 99.6 g anhydrous 2,4,6-trihydroxyphenyl-4'-hydroxybenzyl ketone (375 mmol) and the resulting yellow suspension stirred for 3 h under argon at 25° C., then cooled to 0° C. To this suspension was added the solution of sodium formylsulfate over 2 min and the reaction mixture was stirred for 18 h at 0° C., heated to 80° C., held 30 min to complete gas evolution. To the hot mixture was added over 40 min 732 ml sulfuric acid (36%). After gas evolution had ceased, 2.44 l water-dimethylformamide was distilled at 80° C. and 15 mbar. To the thick suspension was added over 1.5 h at 70° C. 3.99 l of hot water (50° C.). The white suspension was stirred and cooled to 20°

C. overnight, then filtered. The filter cake was washed 3 times with 272 ml water, then dried at 60° C. at 12 mbar overnight to yield 101.9 g of light beige solids. HPLC analysis showed them to contain 93 wt. % genistein for a calculated crude yield of 95%.

EXAMPLE 7

To 138.8 g anhydrous sodium formate (2.0 mol) in 420 ml dimethylformamide at 0° C. was added 306.4 g of a sulfur trioxide-dimethylformamide complex (2.0 mol) in 1.18 l dimethylformamide over 1 h and the reaction held for an additional hour to form a solution of sodium formylsulfate. To 214.2 g anhydrous sodium carbonate (2.0 mol) in 500 ml dimethylformamide was added 208.2 g anhydrous 2,4,6-trihydroxyphenyl-4'-hydroxybenzyl ketone (800 mmol) in 675 ml dimethylformamide and the resulting yellow suspension stirred for 2 h under argon at 25° C., then cooled to 0° C. To this suspension was added the solution of sodium formylsulfate over 20 min, followed by a 200 ml wash of dimethylformamide. The reaction mixture was stirred for 4 h at 0° C., heated over 1 h to 60° C., then held at 60° C. for 1 h to complete gas evolution. To the hot mixture was added over 10 min 197 ml sulfuric acid (30%) to reach pH 4. After gas evolution had ceased, 2.08 l water-dimethylformamide was distilled at 75–85° C. and 60 mbar, then 4.4 water was added at 90° C. over 1 h. The suspension was stirred at 90° C. for 1 h, cooled to 35° C. over 3 h, held for 1 hour, then filtered. The filter cake was washed twice with 200 ml water (40° C.), twice with 200 ml water (20° C.), then with 200 ml ethanol-water (50%) to yield 265.5 g of wet solids. HPLC analysis showed them to contain 202.4 g of 99% genistein for a calculated crude yield of 95%. The moist crystals were dissolved in 5.0 l ethanol at 80° C., filtered, then the solution was concentrated in vacuo to remove 4.38 l ethanol. The resulting suspension was cooled to –10° C. over 3 h, held for 1 h, then filtered. The filter cake was washed twice with ethanol at 0° C. (127 ml each), then dried at 60° C. and 12 mbar for 16 h to give 182.2 g of genistein. HPLC analysis of the product showed 99.2 wt. % genistein. The yield is therefore 85% overall.

What is claimed is:

1. A process for the preparation of 2H-isoflavones of formula I which process comprises the reaction of a 2-hydroxyaryl alkyl ketone of formula II in the presence of a base with a formic-sulfuric anhydride salt of formula III and which reaction is followed by neutralization, wherein formula I is

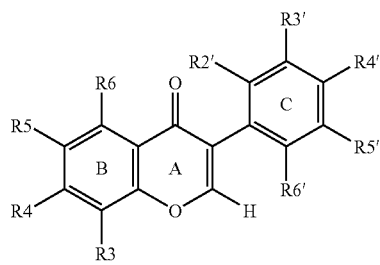

wherein

R3 is hydrogen, hydroxyl or alkoxyl, alkyl, substituted alkyl, or unsaturated alkyl, when R3 is not hydrogen or hydroxyl then the atoms comprising the substituent may comprise a heterocyclic ring of oxygen and carbon atoms attached to position 4 of the ring which rings may be saturated or unsaturated and optionally substituted with alkyl groups;

R4 is hydrogen, hydroxy or alkoxyl, when R4 is alkoxyl then the elements of the substituent may comprise a heterocyclic ring of carbon and oxygen atoms attached to positions 3 or 5 which may be saturated or unsaturated and optionally substituted with alkyl groups;

R5 is hydrogen, hydroxyl, alkoxyl, alkyl, substituted alkyl, or unsaturated alkyl, when R5 is not hydrogen or hydroxyl then the atoms of the substituent may comprise a heterocyclic ring of carbon and oxygen atoms attached to the ring at position 4 to form saturated or unsaturated rings such methylenedioxy or dihydofuran, dihydropyran, or pyrene rings which rings themselves may be substituted with alkyl groups;

R6 is hydrogen, hydroxyl, alkoxyl, alkyl or substituted alkyl;

R2' is hydrogen, hydroxyl, alkoxyl, alkyl, substituted alkyl, or unsaturated alkyl;

R3' is hydrogen, hydroxyl, alkoxyl, alkyl, substituted alkyl or unsaturated alkyl, when R3' is not hydrogen or hydroxyl, the atoms of the substituent may comprise a heterocyclic ring of carbon and oxygen atoms attached to position 2' or 4' which ring maybe saturated or unsaturated and may be substituted with alkyl groups;

R4' is hydrogen, hydroxyl, or alkoxyl, when R4' is not hydrogen or hydroxyl the elements of the substituent may comprise a heterocyclic ring of carbon and oxygen which are attached at position 3' or 5', which ring may be saturated or unsaturated and is optionally substituted with alkyl groups;

R5' is hydrogen, hydroxyl, alkoxyl, alkyl, substituted alkyl or unsaturated alkyl, when R5' is not hydrogen or hydroxyl, the atoms of the substituent may comprise a heterocyclic ring of carbon and oxygen atoms attached to position 4', which ring may be saturated or unsaturated and may be substituted with alkyl groups;

R6' is hydrogen, hydroxyl, alkoxyl, alkyl, substituted alkyl, or unsaturated alkyl;

formula II is

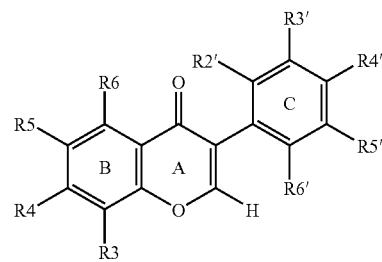

wherein the substituents have the meaning as defined above; and formula III is

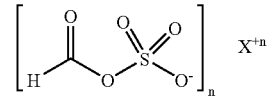

wherein
X is a metallic cation, ammonium, an amine salt, salt of a heterocyclic base, quaternary ammonium or phosphonium salt including polymeric or polymer bound forms thereof;
n is an average number of 1 to 4.

2. A process according to claim 1 which comprises
(a) reaction of a mixture of a 2-hydroxyaryl alkyl ketone of formula II with a suitable base in a suitable solvent,
(b) reaction of the ketone salt with a preformed salt of formic-sulfuric anhydride of formula III,
(c) neutralizing the reaction mixture with a suitable acid, and
(d) separating and isolating the isoflavone.

3. The process according to claim 1 wherein the base is selected from the group consisting of sodium carbonate, potassium carbonate, calcium carbonate, triethylamine, tributylamine, and di-isopropylethylamine.

4. The process according to claim 1 wherein the counterion of the formic-sulfuric anhydride of formula III is sodium, potassium, calcium, triethylammonium, tributylammonium or di-isopropylethyl ammonium.

5. The process according to claim 1 wherein the process is performed at a temperature in the range of from −20° C. to +20° C., with an optional heating of up to 100° C.

6. The process according to claim 1 wherein R4 and R6 are hydroxyl.

7. The process according to claim 1 wherein R4, R6 and R4' are hydroxyl.

8. The process according to claim 2 wherein the base is selected from the group consisting of sodium carbonate, potassium carbonate, calcium carbonate, triethylamine, tributylamine, and di-isopropylethylamine.

9. The process according to claim 2 wherein the counterion of the formic-sulfuric anhydride of formula III is sodium, potassium, calcium, triethylammonium, tributylammonium or di-isopropylethyl ammonium.

10. The process according to claim 3 wherein the counterion of the formic-sulfuric anhydride of formula III is sodium, potassium, calcium, triethylammonium, tributylammonium or di-isopropylethyl ammonium.

11. The process according to claim 8 wherein the counterion of the formic-sulfuric anhydride of formula III is sodium, potassium, calcium, triethylammonium, tributylammonium or di-isopropylethyl ammonium.

12. The process according to claim 2 wherein the process is performed at a temperature in the range of from −20° C. to +20° C., with an optionally heating of up to 100° C.

13. The process according to claim 3 wherein the process is performed at a temperature in the range of from −20° C. to +20° C., with an optionally heating of up to 100° C.

14. The process according to claim 4 wherein the process is performed at a temperature in the range of from −20° C. to +20° C., with an optionally heating of up to 100° C.

15. The process according to claim 2 wherein the solvent is an ether, an ester, or an amide.

16. The process according to claim 2 wherein R4 and R6 are hydroxyl.

17. The process according to claim 3 wherein R4 and R6 are hydroxyl.

18. The process according to claim 2 wherein R4, R6 and R4' are hydroxyl.

* * * * *